United States Patent
Forrest

(10) Patent No.: US 12,377,940 B1
(45) Date of Patent: Aug. 5, 2025

(54) BALLAST TANK DECONTAMINATION SYSTEM AND METHOD FOR WATERSPORTS BOATS

(71) Applicant: Correct Craft IP Holdings, LLC, Orlando, FL (US)

(72) Inventor: Kris Forrest, San Martin, CA (US)

(73) Assignee: CORRECT CRAFT IP HOLDINGS, LLC, Orlando, FL (US)

( * ) Notice: Subject to any disclaimer, the term of this patent is extended or adjusted under 35 U.S.C. 154(b) by 606 days.

(21) Appl. No.: 17/839,886

(22) Filed: Jun. 14, 2022

Related U.S. Application Data

(63) Continuation-in-part of application No. 17/227,465, filed on Apr. 12, 2021, now abandoned.

(60) Provisional application No. 63/140,100, filed on Jan. 21, 2021, provisional application No. 63/009,938, filed on Apr. 14, 2020.

(51) Int. Cl.
| | |
|---|---|
| *B63B 57/02* | (2006.01) |
| *A61L 2/04* | (2006.01) |
| *A61L 2/24* | (2006.01) |
| *A61L 2/26* | (2006.01) |
| *B63B 13/00* | (2006.01) |
| *B63B 34/70* | (2020.01) |
| *B63B 57/00* | (2006.01) |

(52) U.S. Cl.
CPC ............... *B63B 57/02* (2013.01); *A61L 2/04* (2013.01); *A61L 2/24* (2013.01); *A61L 2/26* (2013.01); *B63B 13/00* (2013.01); *B63B 34/70* (2020.02); *A61L 2202/14* (2013.01); *A61L 2202/15* (2013.01); *A61L 2202/17* (2013.01); *A61L 2202/23* (2013.01); *B63B 2057/005* (2013.01)

(58) Field of Classification Search
CPC ... B63B 57/02; B63B 34/70; B63B 2057/005; B63B 13/00; A61L 2/04; A61L 2/24; A61L 2/26; A61L 2202/14; A61L 2202/15; A61L 2202/17; A61L 2202/23
See application file for complete search history.

(56) References Cited

U.S. PATENT DOCUMENTS

| | | | |
|---|---|---|---|
| 5,711,819 A | | 1/1998 | Miyasaki |
| 5,932,112 A | * | 8/1999 | Browning, Jr. ........... C02F 1/20 210/764 |
| 8,798,825 B1 | * | 8/2014 | Hartman ................. B63B 13/00 701/36 |
| 2004/0007255 A1 | | 1/2004 | Labib |
| 2009/0152183 A1 | | 6/2009 | Stewart |
| 2009/0321365 A1 | | 12/2009 | Eriksson |
| 2014/0021143 A1 | | 1/2014 | Hummer |

(Continued)

OTHER PUBLICATIONS

Colorado Division of Wildlife; ANS Tips for Boats with Ballast Tanks; 2011.

*Primary Examiner* — Stephen P Avila
(74) *Attorney, Agent, or Firm* — Allen, Dyer, Doppelt + Gilchrist, PA

(57) ABSTRACT

One or more spray nozzles are positioned in the ballast tanks of watersports boat to allow application of a hot water spray to the internal surfaces thereof. A water conduit leading between the spray nozzles and a hull connection facilitates supply of water thereto. A pump and heater can be provided on the watersports boat connected in the water conduit to produce the hot water for decontamination onboard. A controller can be used to automate the decontamination regimen.

26 Claims, 5 Drawing Sheets

(56) References Cited

U.S. PATENT DOCUMENTS

| | | |
|---|---|---|
| 2015/0298990 A1 | 10/2015 | Urke |
| 2016/0318593 A1 | 11/2016 | Hummer |
| 2022/0033048 A1 | 2/2022 | Yamamoto |

\* cited by examiner

BALLAST TANK DECONTAMINATION SYSTEM AND METHOD FOR WATERSPORTS BOATS

CROSS-REFERENCE TO RELATED APPLICATIONS

This application is a continuation-in-part of U.S. Nonprovisional patent application Ser. No. 17/227,465, filed on Apr. 12, 2021, which claims the benefit of U.S. Provisional Patent Application Ser. No. 63/009,938, filed on Apr. 14, 2020, and U.S. Provisional Patent Application Ser. No. 63/140,100, filed on Jan. 21, 2021, the contents of which applications are herein incorporated by reference in their entirety.

FIELD OF THE INVENTION

The present invention relates to watersports boats having ballast tanks for altering wake characteristics, and more particularly, to systems and methods for decontaminating such tanks.

BACKGROUND OF THE INVENTION

With the rising popularity of watersports like wakeboarding and wakesurfing, it has become common to add ballast to watersports boats in order to increase the size and optimize the shape of the generated wake. While solid ballast is sometimes used, water is most used for ballasting. The water is generally pumped into one or more tanks onboard the boat at the beginning of a day on the water. These tanks are then pumped out or otherwise drained afterwards. As used herein, the term "tank" is used to describe both hard tanks (e.g., made of rigid plastic, fiberglass or metal) and soft tanks (e.g., flexible plastic or fabric "ballast bags") unless one or the other is specified.

While ballast systems have been great for watersports boats from an operational perspective, there is significant concern that residual water in ballast tanks offer an opportunity for the transfer of aquatic invasive species (AIS), such as *quagga* and zebra mussels, between bodies of water. Since AIS can be microscopic (e.g., mussels during the larval stage), filtering is usually insufficient to prevent their introduction into ballast tanks. To help minimize this risk, various civil authorities require watersports boats equipped with ballast tanks to undergo a special decontamination procedure before each launch.

This decontamination procedure generally entails pumping hot water from some external source into the ballast tanks (and through any associated piping) for a predetermined time period to kill any lingering AIS. While effective at addressing the AIS problem, this type of decontamination procedure is often problematic for a number of reasons. For instance, the externally supplied water is often heated too hot for temperature sensitive components within the ballast system, such as pumps and seals, resulting in costly and premature equipment failures. Additionally, very few bodies of water are provided with decontamination systems at launching sites, and the time needed to wait for and then undergo the decontamination is often excessive.

SUMMARY OF THE INVENTION

In view of the foregoing, it is an object of the present invention to provide improved ballast tank decontamination systems and related methods. According to an embodiment of the present invention, a watersports boat comprises a hull, a first ballast tank carried by the hull having a first internal surface, and a ballast tank decontamination system. The decontamination system includes a first water connection, a first water conduit extending from the first water connection to the at least one ballast tank, a first heater connected in the water conduit between the water connection and the ballast tank, at least one first spray nozzle connected to the water conduit and positioned in the first ballast tank, the at least one first spray nozzle being configured to direct water spray over the first internal surface, and a first pump connected in the water conduit between the water connection and the at least one first spray nozzle and operable to pump water therebetween.

According to an aspect of the present invention, the ballast tank decontamination system further includes a first heater connected in the water conduit between the water connection and the ballast tank, and a first pump connected in the water conduit between the water connection and the at least one first spray nozzle and operable to pump water therebetween.

According to a method aspect, a method of ballast tank decontamination for a watersports boat comprises delivering a heated water spray over an internal surface of a ballast tank of the watersports boat through at least one spray nozzle positioned in the ballast tank to eliminate an aquatic invasive species.

These and other objects, aspects and advantages of the present invention will be better appreciated in view of the drawings and following detailed description of preferred embodiments.

DETAILED DESCRIPTION OF PREFERRED EMBODIMENTS

Figure 1:
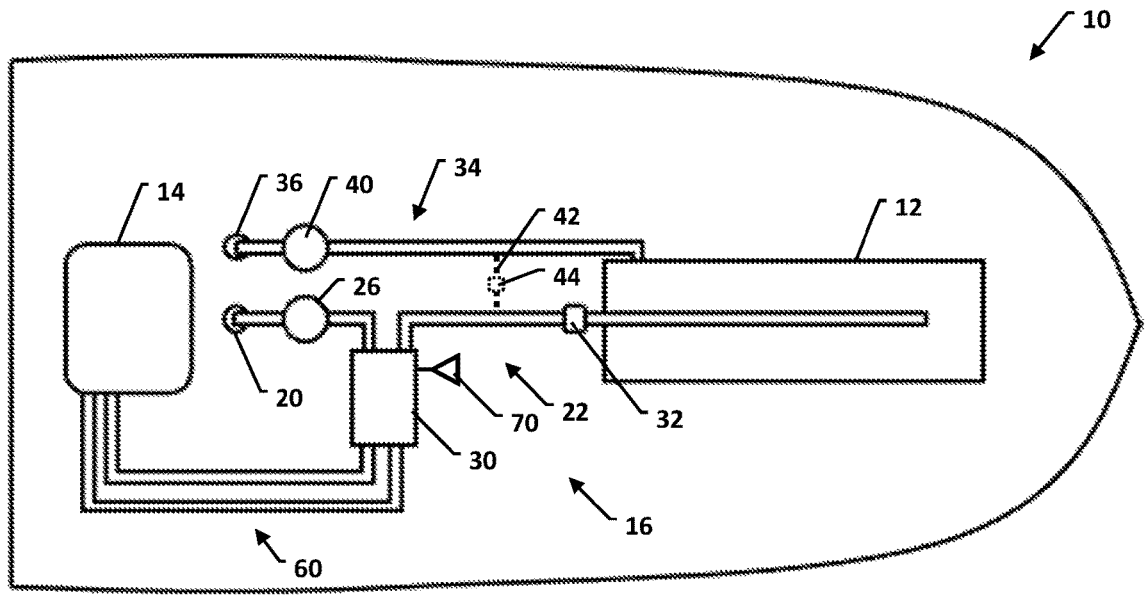
FIG. 1 is a schematic overview of a watersports boat with a ballast tank decontamination system, according to an embodiment of the present invention.
Figure 2:
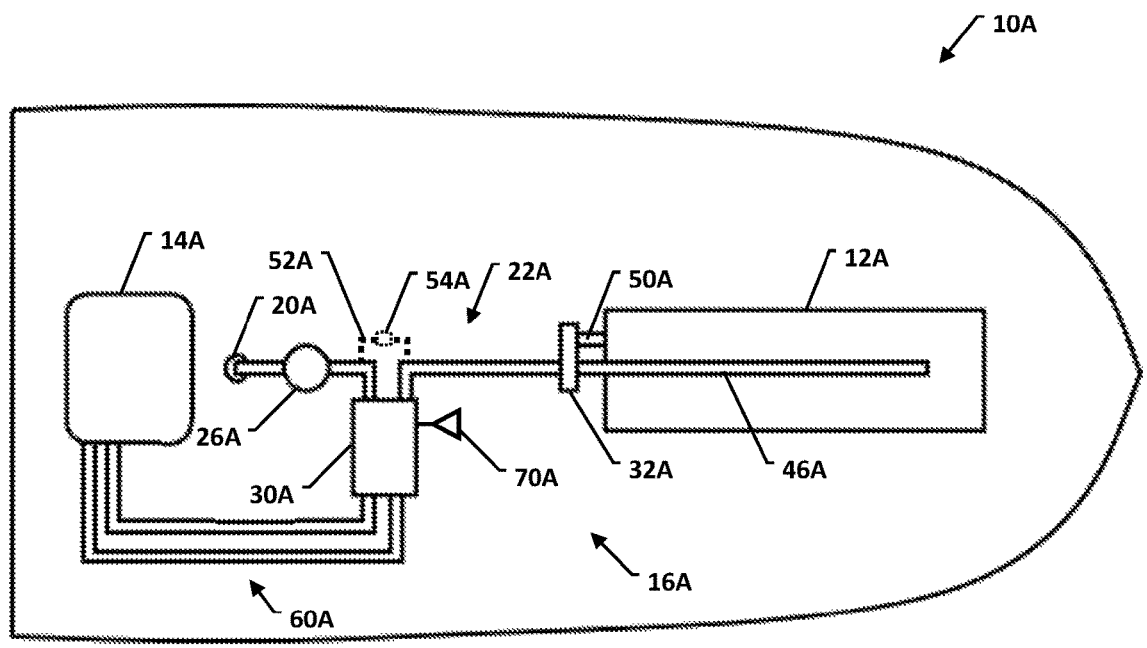
FIG. 2 is a schematic overview of a watersports boat with a ballast tank decontamination system, according to another embodiment of the present invention.

Referring to FIGS. 1 and 2, watersports boats 10, 10A are equipped with at least one ballast tank 12, 12A and an engine 14, 14A. Both boats 10, 10A include a ballast tank decontamination system 16, 16A having a water connection 20, 20A and a water conduit 22, 22A leading from the water connection 20, 20A to the ballast tank 12, 12A to one or more spray nozzles 24, 24A positioned in the ballast tank 12, 12A (see FIGS. 3 and 4).

In each embodiment, a pump 26, 26A and a heater 30, 30A are connected in the water conduit 22, 22A between the water connection 20, 20A and the spray nozzles 22, 22A. Each pump 26, 26A is operable to pump water through the conduit 22, 22A from the water connection 20, 20A to the heater 26, 26A and from the heater 30, 30A to the spray nozzles 24, 24A. Heated water from the nozzles 24, 24A is sprayed over the internal surface of the ballast tank 12, 12A. A valve arrangement 32, 32A is operable to initiate and secure the spray.

In the watersports boat 10, the ballast tank 12 is filled and drained during normal operation through a separate water conduit 34 extending between a fill/drain connection 38 of the ballast tank 12 and a separate water connection 36. The fill/drain conduit 32 has its own pump 40 located therein. This arrangement can allow the ballast tank decontamination system 16 to be more readily retrofit into existing watersports boats. To allow the system 16 to be used to flush the fill and drain conduit 32, a junction line 42 can be included between the conduits 22, 34 with a control valve 44.

In the watersports boat 10A, the water conduit 22A and the pump 26A are also used to fill and drain the ballast tank 12A. Between the valve arrangement 32A, the water conduit 22A is divided into a first branch 46A leading to the spray nozzles 24A and a second branch 50A leading to a fill/drain connection 38A. The valve arrangement 32A is configured to selectively route flow to either the spray nozzles 24A or the fill/drain connection 38A.

In the system 12A, the pump 26A can simply be reversed to backflush the water conduit 22A between the heater 30A and the water connection 20A with hot water. A bypass line 52A with a control valve 54A can be included to allow the heater 30A to be bypassed when filling and draining the ballast tank 12A during normal operation.

For clarity of illustration, only a single ballast tank 12, 12A is depicted in FIGS. 1 and 2. It will be appreciated, however, that the ballast tank decontamination systems 16, 16A could readily be configured to service multiple ballast tanks. For instance, the system 16, 16A components could simply be duplicated or separate branches of the water conduit 22A for each ballast tank could be included for each ballast tank.

Figure 3:
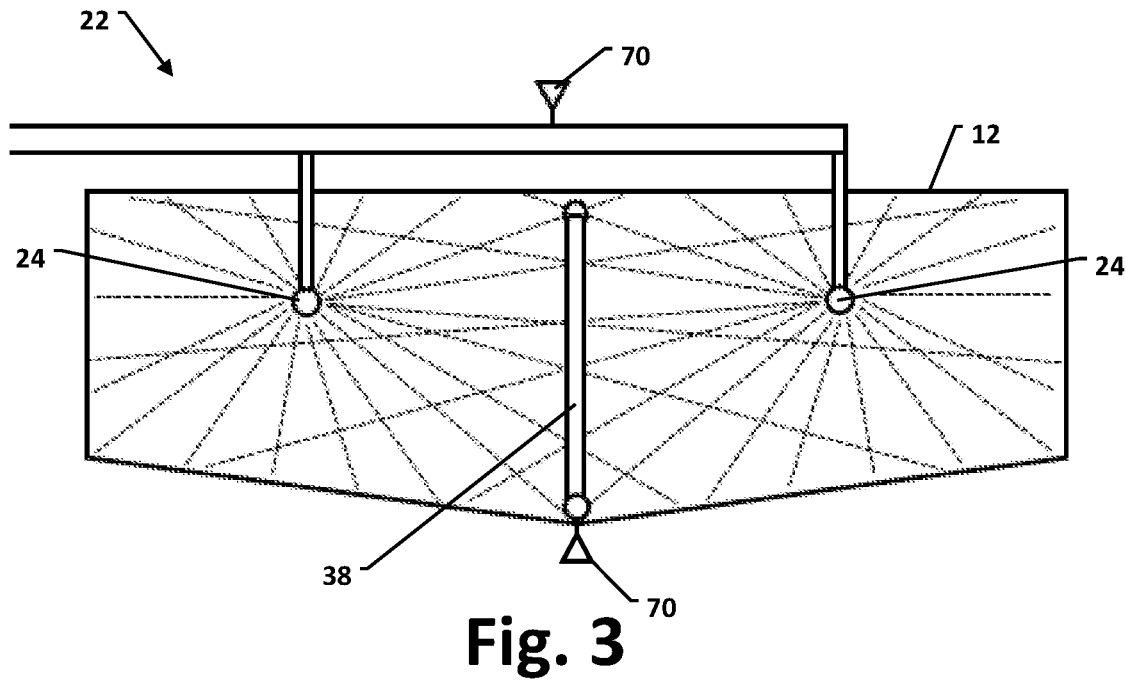
FIGS. 3 and 4 are schematic sectional views of ballast tanks including spray nozzles of the ballast tank decontamination system of FIG. 1 or FIG. 2.
Figure 4:
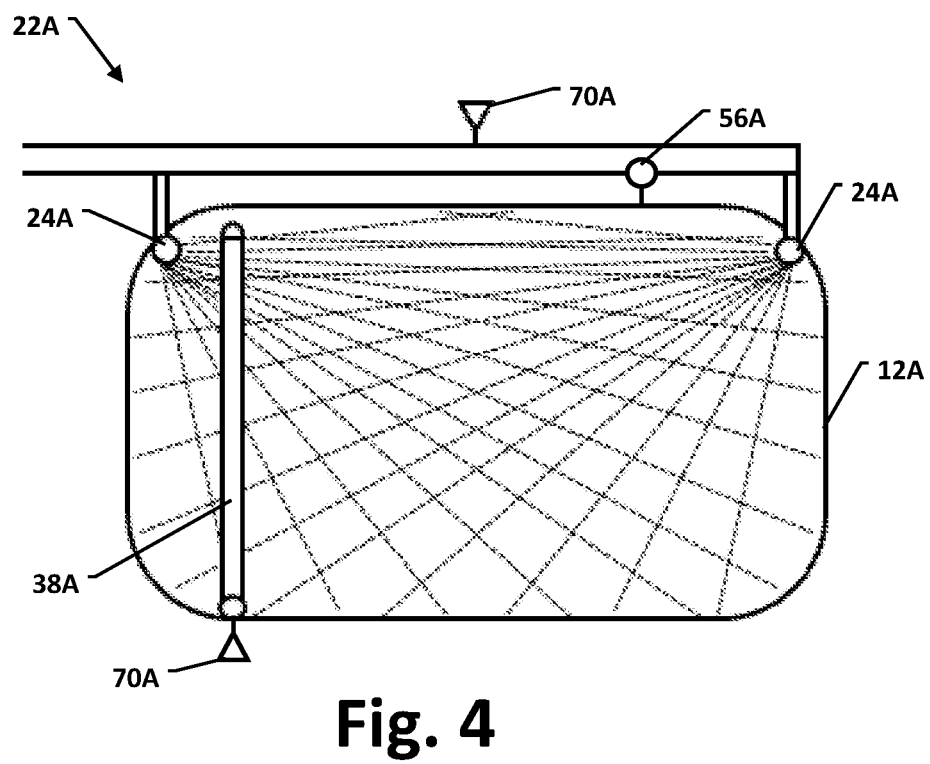

As noted above, the term "tank" as used herein is not necessarily limited to rigid tanks but could apply to soft tanks or "ballast bags," as well; FIG. 3 schematically depicts a rigid tank, while FIG. 4 schematically depicts a soft tank-though either or both types of tanks could be used with either system 12, 12A. Where a soft tank is used, a pressure sensor 56A can be used to control the introduction of air into the tank to ensure an advantageous geometry for decontamination spray.

Additionally, the invention is not limited to any particular size or geometry of tank, however the number, configuration and placement of spray nozzles is advantageously selected to allow the entirety of the interior surface of the tank to be sprayed. Nozzles with omni-directional spray patterns and/or rotating or pivoting nozzles could advantageously be employed to facilitate tank coverage. The use of a hot water spray, versus completely filling the ballast tank with water, can greatly reduce the time and energy required for effective decontamination. This could also be applied to other contained volumes on recreational watercraft that are in fluid communication with the surrounding water; for example, live wells on fishing boats.

The water connection 20, 20A advantageously includes through-hull connection below the waterline of the watersports boat 10, 10A with an associated solenoid-operated hull valve. Alternately, or in addition to, such a connection, a connection above the waterline could be included for ease of connection to an external water source (e.g., a hose). The water connection preferably includes a standard hose fitting allowing a hose to be easily threaded therein for supply from an external source.

As will be appreciated, the water conduit 22, 22A can be divided into several sections in fluid communication, as between the water connection 20, 20A and the pump 26, 26A, the pump 26, 26A and the heater 30, 30A, the heater 30, 30A and the valve arrangement 32, 32A and so on. In some embodiments of the present invention, the water conduit could simply lead directly from a water connection to the spray nozzle(s) in the ballast tank(s). While such embodiments would require pressurized, heated water from an external source for supplying to the spray nozzles in the ballast tank, the time required for effective decontamination could still be greatly abbreviated relative to typical decontamination procedures. Such a procedure would typically be performed with the watersports boat on a trailer.

The pump 26, 26A is preferably a reversible pump. Internal pump components are advantageously selected for compatibility with the hot water temperatures achieved by the decontamination system 12, 12A. While the use of hot water is believed to be preferable from an environmental standpoint, it will be appreciated that embodiments of the present invention could be used to deliver a biocidal spray or other chemical effective to safely eliminate AIS.

The heater 30, 30A preferably includes an electric heating element supplemented by heat exchange with an engine conduit loop 56, 56A going to and from an engine 14, 14A heat source. The heater is 30, 30A is dimensioned to hold a predetermined volume of water sufficient to decontaminate the ballast tank 12, 12A via spray and, preferably, to subsequently backflush the water conduit 22, 22A through the pump 26, 26A to the water connection 20, 20A. For most watersports boats, a tank volume in the range of approximately 3 to 6 gallons, and more preferably approximately 4 to 5 gallons, should generally be sufficient.

The heat capacity of the heater 30, 30A is preferably sufficient to heat the water therein to a temperature of greater than approximately 120 degrees Fahrenheit (F), and more preferably, greater than approximately 130 degrees F. in less than 30 minutes. The heater element of the heater 30, 30A could be an AC or DC heater resistance heater element. Where AC power is used, the heater 30, 30A could advantageously include a dedicated inverter.

Any suitable engine heat source, or combination thereof, could be used, with non-limiting examples including engine coolant, engine oil, engine exhaust and/or transmission oil. Intermediate heat exchange could occur between another fluid exposed to the engine heat source and the loop 60, 60A leading to the heater 30, 30A or the loop 60, 60A could exchange heat directly with the heat source.

The valve arrangement 32, 32A preferably includes one or more solenoid-operated valves. In embodiments where the control valve 44 or the control valve 54A are utilized, these are preferably also solenoid-operated.

Figure 5:
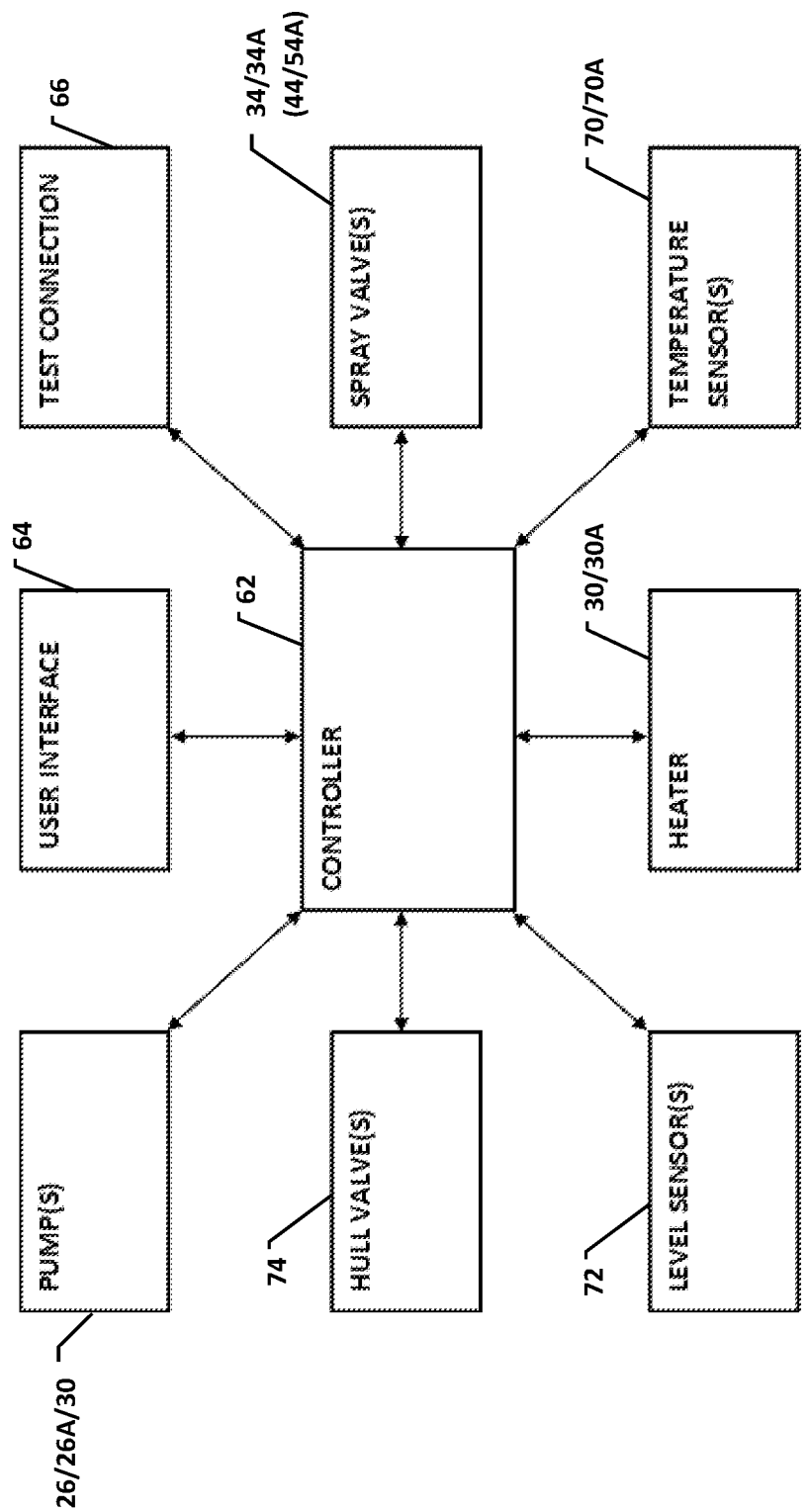
FIG. 5 is an organization view of electronically controlled components of the ballast tank decontamination system of FIG. 1 or FIG. 2.

Referring also to FIG. 5, the operation of the decontamination system 12, 12A is preferably implemented automatically via controller 62. The controller 62 preferably includes one or more microprocessors and machine-readable memory configured with software instructions to execute various system functions according to a predetermined regimen, as will be explained in greater detail below. It will be appreciated that various controller functions could be distributed to different microprocessors or other digital and/or analog control circuits located throughout the watersports boat 10, 10A.

The system preferably also includes a user interface 64 for initiating ballast tank decontamination and displaying decontamination status, including verification of completed decontamination. A touch screen display is one non-limiting example of a suitable user interface. A test connection 66 can advantageously be supplied for allowing auditability of proper operation of the controller 62 and other electrical system components.

The controller 62 is preferably in signal communication with one or more temperature sensors 70, 70A, which allow verification that water temperatures within predetermined ranges are being achieved. Exemplary sensor locations include at the heater 30, 30A, proximate the supply of water from the conduit 22, 22A to the nozzles 24, 24A and/or proximate water exit points. Lower thresholds can be set to ensure sufficient heat to kill AIS, while upper thresholds can be set to avoid damage to temperature sensitive system components. Additionally, sensed water temperature during spray can be used to control spray time. Generally, supplying water from the heater 30, 30A to the nozzles 34, 34A in a range of 120 F to 140 F is preferred.

The controller 62 advantageously also receives inputs from one or more level sensors 72. For example, level sensors can be used to verify that the ballast tank(s) are adequately empty before spray operations commence to ensure that internal surfaces will not be blanketed by excess cold water.

The controller 62 is configured to operate the valve arrangements 34, 34A to start and secure spray, as well as the junction and bypass control valves 44, 54A in embodiments so equipped. The controller 62 is also configured to control the heater 30, 30A, the pumps 26, 26A, 30 and hull valves 74 as needed in connection with decontamination operations, as will be explained in greater detail below. Where the heater 30, 30A includes an electric heating element powered via an inverter, the controller 62 is preferably also configured to monitor and controller inverter operation.

Figure 6A:
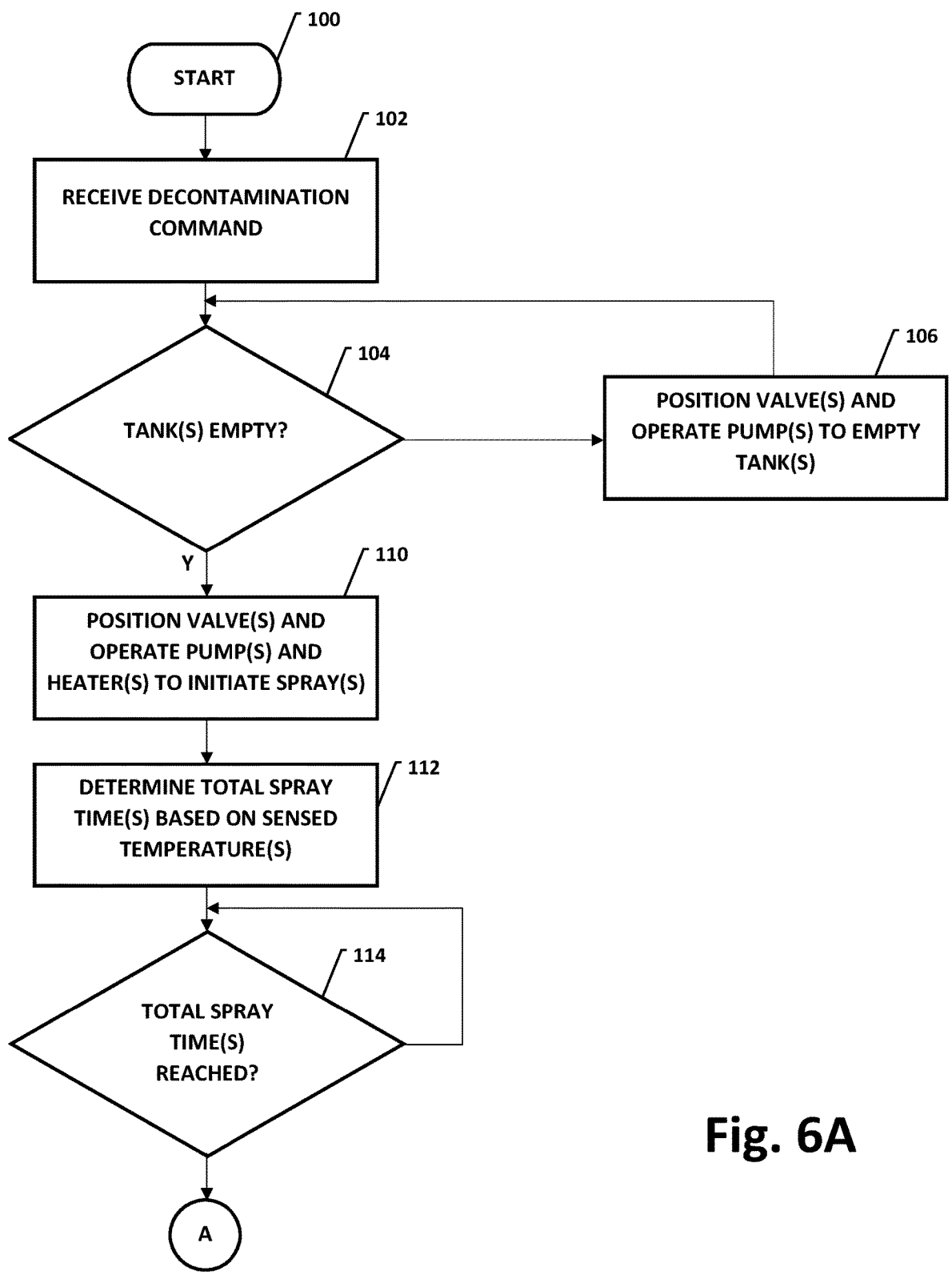
FIGS. 6A and 6B are a flow diagram of operation of the ballast tank decontamination system of FIG. 1 or FIG. 2.
Figure 6B:
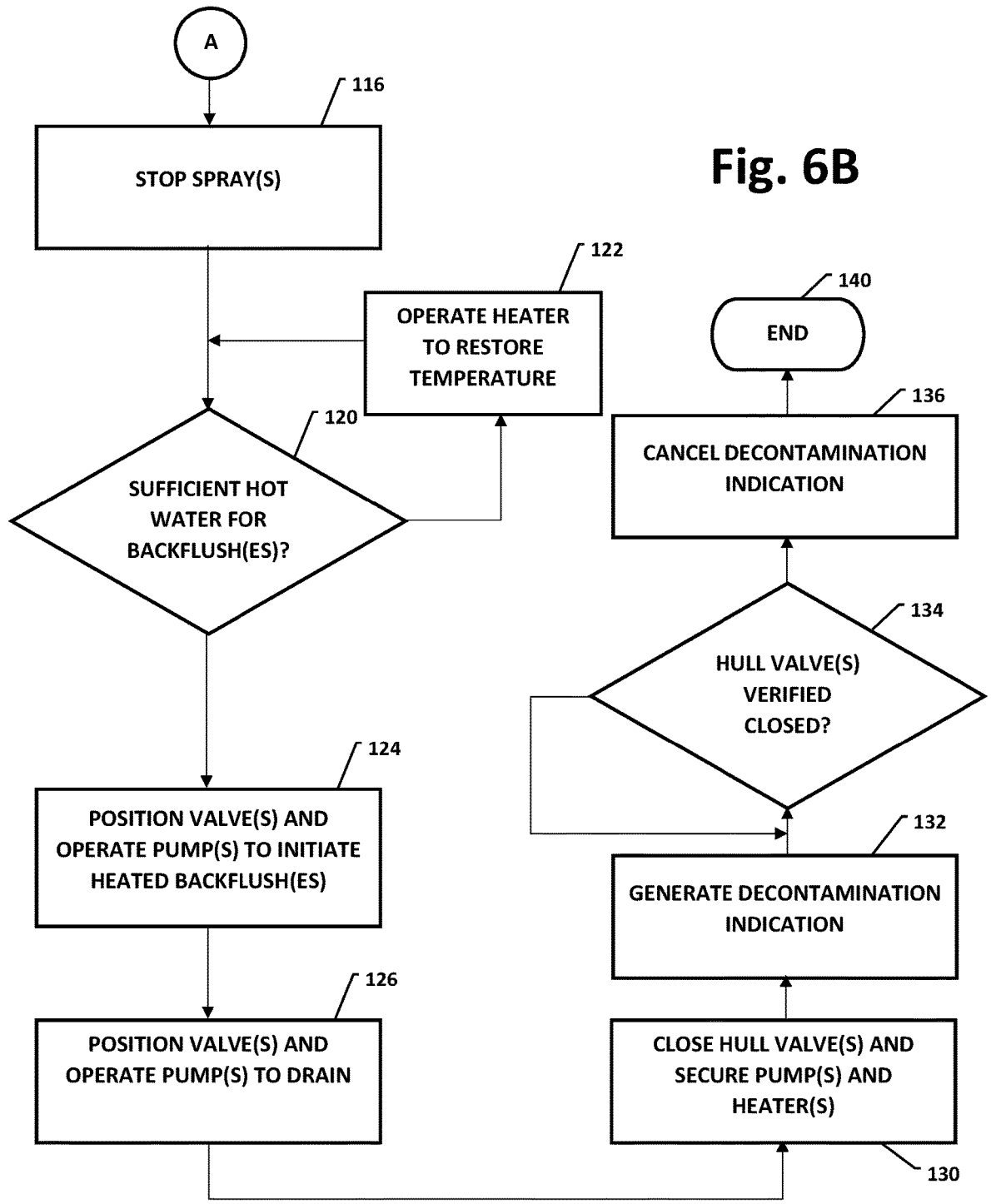

Referring to FIGS. 6A and 6B, the decontamination regimen begins at block 100 in connection with receipt of a decontamination command by the controller 62 at block 102. The command can be generated by user input via the user interface 64. Alternately, the command could be automatically generated based on circumstances—for instance, in connection with receiving a command to fully drain the ballast tank(s). The controller 62 could also provide prompts to a user to initiate decontamination.

At block 104, the controller 62 determines whether the ballast tank(s) are sufficiently empty for decontamination. If not, then the controller 62 positions valve(s) and operate(s) pumps as necessary at block 106 to empty the tank(s). For instance, in the system 16, the controller would ensure the valves 32 and 44 were closed, and the hull valve associated with the water connection 36 was open and operate the pump 40 in reverse to drain the tank 12. In the system 16A, the controller 62 would position the valve arrangement 32A to connect with the second branch 50A, operate the valve 54A to bypass the heater 30A, open the hull valve associated with the water connection 20A and operate the pump 26A in reverse to the drain the tank 12A.

With tanks sufficiently empty, the controller 62 positions valve(s) and operate(s) pump(s) and heater(s) to initiate sprays(s) at block 110. In the system 12 example, the controller 62 would operate the heater 30 until the water therein achieved the desired set point. The controller 62 would then ensure the hull valve at the water connection 20 was open, the junction valve 44 was closed and the valve 32 was open. The pump 26 would then be operated to initiate spray to the tank 12. In the system 12A, the controller 62 would operate the heater 30A as just described and, once the temperature set point was reached, ensure the hull valve of the water connection 20A was open, the valve arrangement 32A was positioned to connection with the first branch 46A, the bypass valve 54A was shut and then operate the pump 26A to initiate spray.

Once spray is initiated, the spray could be continued for a fixed predetermined time once the temperature set point was reached or, at block 112, the controller 62 could adjust the spray time based on actual sensed temperature while spraying. This could include temporarily ceasing spray, if necessary, to allow temperature to be restored. In any case, the controller 62 would continue spray until determining that the total required spray time had been reached at block 114.

Once the total required spray time had been reached, the controller 62 would stop spray(s) at block 116, typically by securing the associated pump(s). If the decontamination regimen includes backflushing, the controller 62 determines at block 120 if there is sufficient hot water for backflushing; for instance, based on the water temperature in the heater(s). If there is not sufficient hot water, the controller 62 could operate the heater(s) at block 122 to restore water temperature.

Once there is sufficient hot water for backflushing, the controller 62 positions valve(s) and operates pump(s) to initiate backflush(es) at block 124. For instance, in the system 12, the controller 62 would backflush to the hull connection 20 by reversing the pump 26. The controller 62 could subsequently backflush the water conduit 34 by closing the spray valve 32, opening the junction valve 42 and the hull valve at connection 36, and operating the pump 26 in forward and/or the pump 40 in reverse. In the system 12A, the controller 62 would only need to operate the pump 26A in reverse to backflush to the hull connection 20A.

After backflushing is complete, if it desired to empty residual water from spraying the ballast tank(s), then the controller 62 position valve(s) and operates pump(s) to drain the tank(s) at block 126. In the system 12 example, the controller 62 would close the junction valve 44, ensure the hull valve of the connection 36 was open, and operate the pump 40 in reverse to drain the tank 12. With system 12A, the controller 62 would position the valve arrangement 32A to connect the second branch 50A, open the bypass valve 54A and operate the pump 26A in reverse.

With backflushing complete, all hull valves(s) are closed and the operation of pump(s) and heater(s) are secured by the controller 62 at block 130. With the ballast tanks decontaminated and isolated from the re-introduction of surrounding water, the controller generates a decontamination indication at block 132. This indication could be used as proof of decontamination to allow a boater to bypass use of an external decontamination station when subsequently launching.

To ensure the integrity of the decontamination indication, the controller 62 only maintains the indication for as long as it can positively verify that the hull valve(s) remain closed at block 134. If the controller 62 detects that hull valve(s) have been reopened (or otherwise loses the capacity to reasonably verify closure), the decontamination indication is canceled at block 136. The regimen concludes at block 140 but can be repeated as often as desired.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

What is claimed is:

1. A watersports boat comprising:
   a hull;
   a first ballast tank carried by the hull having a first internal surface;
   a ballast tank decontamination system system including:
      a first water connection;
      a first water conduit extending from the first water connection to the first ballast tank; and
      at least one first spray nozzle connected to the first water conduit and positioned in the first ballast tank, the at least one first spray nozzle being configured to spray water from the first water connection over the first internal surface;
   a controller configured with program instructions to operate the ballast tank decontamination system to deliver the water spray through the at least one first spray nozzle according to a predetermined regimen and at a temperature sufficient to decontaminate the first ballast tank, and to generate a decontamination indication after delivering the water spray.

2. The watersports boat of claim 1, wherein the ballast tank decontamination system further includes:
   a first heater connected in the water conduit between the water connection and the ballast tank; and
   a first pump connected in the water conduit between the water connection and the at least one first spray nozzle and operable to pump water therebetween.

3. The watersports boat of claim 2, further comprising an engine carried by the hull;
   wherein the first heater includes a heat exchanger receiving a heat input from an engine conduit loop extending between an engine heat source and the first heater.

4. The watersports boat of claim 3, wherein the engine heat source includes at least one of: engine coolant, engine oil, engine exhaust and transmission oil.

5. The watersports boat of claim 3, wherein the first heater further includes an electric heating element.

6. The watersports boat of claim 2, wherein the first heater further includes an electric heating element.

7. The watersports boat of claim 2, wherein the first water conduit includes a first branch leading to the at least one first spray nozzle and a second branch leading to a fill/drain connection of the first ballast tank separate from the at least one first spray nozzle.

8. The watersports boat of claim 7, wherein the ballast tank decontamination system a first valve arrangement operable to selectively route flow in the first water conduit to the first ballast tank through either the first or second branch.

9. The watersports boat of claim 8, wherein the first valve arrangement is between the first pump and the first ballast tank.

10. The watersports boat of claim 9, wherein the first valve arrangement is between the first heater and the first ballast tank.

11. The watersports boat of claim 1, wherein the ballast tank decontamination system further includes at least one temperature sensor operable to sense a water temperature in the first water conduit.

12. The watersports boat of claim 11, wherein the predetermined regimen includes determining a total spray time based on the sensed water temperature.

13. The watersports boat of claim 11, wherein the predetermined regimen includes determining whether the sensed water temperature in the first heater has reached a predetermined level before initiating spray.

14. The watersports boat of claim 1, wherein the controller is further configured with program instructions to perform a backflushing routine.

15. The watersports boat of claim 14, wherein the controller is further configured with program instructions to perform the backflushing routine after delivering the water spray.

16. The watersports boat of claim 1, wherein the ballast tank decontamination system further includes a first hull valve operable to close the first water connection; and
   wherein the controller is further configured with program instructions to cancel the decontamination indication if the first hull valve is subsequently not verified to be closed.

17. The watersports boat of claim 1, wherein the at least one first spray nozzle includes a plurality of first spray nozzles.

18. The watersports boat of claim 1, wherein the first ballast tank is a hard tank.

19. The watersports boat of claim 1, wherein the first ballast tank is a soft tank.

20. The watersports boat of claim 1, wherein the first water connection includes a through hull connection below a waterline of the hull.

21. A watersports boat comprising:
   a hull;
   a first ballast tank carried by the hull having a first internal surface; and
   a ballast tank decontamination system including
      a first water connection,
      a first water conduit extending from the first water connection to the first ballast tank,
      a hot water tank coupled inline with the first water conduit and configured to hold a predetermined volume of water at a temperature sufficient to decontaminate the first ballast tank, and
      at least one first spray nozzle connected to the first water conduit and positioned in the first ballast tank, the at least one first spray nozzle being configured to spray water from the hot water tank over the first internal surface after draining the first ballast tank.

22. The watersports boat of claim 21, further comprising an engine carried by the hull, and wherein the water in the hot water tank is heated by heat from the engine.

23. The watersports boat of claim 21, further comprising an electric heating element configured to heat the water in the hot water tank.

24. A ballast tank decontamination system for a watersports boat comprising a hull and a first ballast tank by the hull having a first internal surface, the system comprising:
   a first water connection;
   a first water conduit extending from the first water connection to the first ballast tank;
   a hot water tank coupled inline with the first water conduit and configured to hold a predetermined volume of water at a temperature sufficient to decontaminate the first ballast tank; and
   at least one first spray nozzle connected to the first water conduit and positioned in the first ballast tank, the at least one first spray nozzle being configured to spray water from the hot water tank over the first internal surface after draining the first ballast tank.

25. The system of claim 24, wherein the watersports boat further comprises an engine carried by the hull, and wherein the water in the hot water tank is heated by heat from the engine.

26. The system of claim 21, further comprising an electric heating element configured to heat the water in the hot water tank.

\* \* \* \* \*